(12) United States Patent
Nam et al.

(10) Patent No.: US 11,529,334 B2
(45) Date of Patent: Dec. 20, 2022

(54) PHARMACEUTICAL COMPOSITION FOR TREATING OR PREVENTING PARKINSON'S DISEASE COMPRISING STT AS AN ACTIVE INGREDIENT

(71) Applicants: GACHON UNIVERSITY OF INDUSTRY—ACADEMIC COOPERATION FOUNDATION, Gyeonggi-do (KR); GIL MEDICAL CENTER, Incheon (KR); UNIVERSITY—INDUSTRY COOPERATION GROUP OF KYUNG HEE UNIVERSITY, Gyeonggi-do (KR)

(72) Inventors: Seung Yoon Nam, Gyeonggi-do (KR); Jinhyuk Lee, Daejeon (KR); Joo-Won Jeong, Gyeonggi-do (KR)

(73) Assignees: GACHON UNIVERSITY OF INDUSTRY-ACADEMIC COOPERATION FOUNDATION, Gyeonggi-do (KR); GIL MEDICAL CENTER, Incheon (KR); UNIVERSITY-INDUSTRY COOPERATION GROUP OF KYUNG HEE UNIVERSITY, Gyeonggi-do (KR)

(*) Notice: Subject to any disclaimer, the term of this patent is extended or adjusted under 35 U.S.C. 154(b) by 328 days.

(21) Appl. No.: 16/852,182

(22) Filed: Apr. 17, 2020

(65) Prior Publication Data
US 2020/0330437 A1 Oct. 22, 2020

(30) Foreign Application Priority Data
Apr. 19, 2019 (KR) .................. 10-2019-0046349

(51) Int. Cl.
  *A61K 31/426* (2006.01)
  *A61P 25/16* (2006.01)
  *A61K 38/46* (2006.01)
  *G01N 33/53* (2006.01)
  *G01N 33/68* (2006.01)

(52) U.S. Cl.
  CPC .......... *A61K 31/426* (2013.01); *A61K 38/465* (2013.01); *A61P 25/16* (2018.01); *G01N 33/53* (2013.01); *G01N 33/6896* (2013.01); *C12Y 301/03048* (2013.01); *G01N 2333/916* (2013.01); *G01N 2800/2835* (2013.01)

(58) Field of Classification Search
None
See application file for complete search history.

(56) References Cited

U.S. PATENT DOCUMENTS

| | | | |
|---|---|---|---|
| 9,833,519 B2* | 12/2017 | Chiorini | A61K 31/519 |
| 2009/0275608 A1* | 11/2009 | Ossovskaya | A61P 31/18 |
| | | | 514/765 |
| 2011/0229883 A1* | 9/2011 | Spur | C12Q 1/6883 |
| | | | 435/6.11 |
| 2015/0368722 A1* | 12/2015 | Chang | C12Q 1/6886 |
| | | | 435/7.1 |
| 2017/0192004 A1* | 7/2017 | Borrebaeck | C40B 40/00 |
| 2017/0269092 A1* | 9/2017 | Kralovics | C07K 16/28 |
| 2017/0275704 A1* | 9/2017 | Stylli | C12Q 1/6886 |
| 2017/0356917 A1* | 12/2017 | Hideshima | G01N 33/573 |

OTHER PUBLICATIONS

Gubellini "Animal models of Parkinson's disease: An updated overview" revue neuro 171:750-761 (machine translation) (Year: 2015).*
Kerkar "What Are The Early Signs Of Parkinson's Disease?" accessed from epainassist.com on May 6, 2022 (Year: 2018).*
Seternes "Dual-specificity MAP kinase phosphatases in health and disease" mol cell res 1866:124-143 (Year: 2019).*
Bermudez "The dual-specificity MAP kinase phosphatases: critical roles in development and cancer" am j phys cell phys 299:189-202 (Year: 2010).*
Remmert et al., "HHblits: lightning-fast iterative protein sequence searching by HMM-HMM alignment," *Nature Methods* 9(2): 173-178 (ePub Dec. 25, 2011).
Trott and Olson, "AutoDock Vina: Improving the speed and accuracy of docking with a new scoring function, efficient optimization and multithreading," *Journal of Computational Chemistry* 31: 455-461 (ePub Jun. 4, 2009).

* cited by examiner

*Primary Examiner* — Adam Weidner
(74) *Attorney, Agent, or Firm* — Klarquist Sparkman, LLP

(57) ABSTRACT

The present invention relates to a pharmaceutical composition comprising a STT compound as an active ingredient for the prevention or treatment of Parkinson's disease. STT showed neuroprotective effect and apoptosis recovery effect in the Parkinson's disease cell model, restored the reduced motility in the MPTP animal model, and was shown to significantly protect dopamine cells, so it can be used for the prevention and treatment of Parkinson's disease.

4 Claims, 20 Drawing Sheets

Specification includes a Sequence Listing.

FIG. 5

DPSP: druggable pocket site prediction $$D_{ij} = \frac{\sum_k^{n_k} w_k}{\sum_i^{n_i} w_i} \cdot \frac{n_k}{n_j} \cdot P_w \cdot L_w \cdot Q_{id} \cdot Freq$$

PHARMACEUTICAL COMPOSITION FOR TREATING OR PREVENTING PARKINSON'S DISEASE COMPRISING STT AS AN ACTIVE INGREDIENT

CROSS-REFERENCES TO RELATED APPLICATION

This patent application claims the benefit of priority under 35 U.S.C. § 119 from Korean Patent Application No. 10-2019-0046349 filed on Apr. 19, 2019, the contents of which are incorporated herein by reference.

FIELD OF THE INVENTION

The present invention relates to a pharmaceutical composition comprising STT (2-(5-Methyl-4-oxo-2-thioxo-1,3-thiazolidin-3-yl) ethanesulfonic acid) as an active ingredient for the prevention or treatment of Parkinson's disease. STT showed neuroprotective effect and apoptosis recovery effect in the Parkinson's disease cell model, restored the reduced motility in the MPTP animal model, and was shown to significantly protect dopamine cells, so it can be used for the prevention and treatment of Parkinson's disease.

DESCRIPTION OF THE RELATED ART

Parkinson's disease is caused by the deficiency of dopamine, a neurotransmitter of the corpus striatum, due to the slow regression of dopamine neurons of the substantia nigra in the basal ganglia. It is a disease exhibiting characteristic motor disorders such as tremer, bradykinesia and rigidity when 70% to 80% or more of the entire corpus striatum is lost. The deficiency of dopamine in the dopamine nervous system is known to be caused by the decreased activity of tyrosine hydroxylase (TH) and aromatic L-amino acid decarboxylase (AADC), the dopamine biosynthesis enzymes, by neuronal cell death.

The number of patients with Parkinson's disease in Korea was 6,565 in 2010, and grew at an annual average rate of 8.7% to 8,888 in 2014. In 2014, the proportion of patients aged 60 years or older was 95.7%, and the prevalence was correlated with the age of the patients. In the case of gender ratio, there were 33,831 males and 52,057 females (Parkinson's disease patients in the last 5 years. Increase in medical expenses, Young Doctors, 2015). The population of Parkinson's disease patients in the seven major countries (US, Japan, France, Germany, Italy, Spain, and UK) was increased by 2.72% per year (about 4.54 million in 2008 and 5.05 million in 2012). The population of Parkinson's disease patients was increased from 1.98 million in 2008 to 2.19 million in 2012 in Asia, and from 820,000 in 2008 to 910,000 in 2012 in Europe (Product and Pipeline Analysis of the Global Parkinson's Disease Therapeutic Market, F&S, 2014). According to the global trend of Parkinson's disease therapeutic agents, the share of dopamine agonist drugs, which had the largest share of 47% in 2011, is expected to decrease to 42% in 2021, and the share of new pipeline drugs is expected to be about 20% in 2021 (R&D Trends: Parkinson's Disease, Datamonitor, 2012).

The tests performed to diagnose Parkinson's disease include 1) PET test, 2) MRI test, and 3) internal disease test. Brain dopamine transporter PET (positron emission tomography) is a test to determine whether dopamine cells are damaged. Parkinson's symptoms induced by causes other than Parkinson's disease can be confirmed by brain dopamine transporter PET. In the cases of drug-induced Parkinson's syndrome, vascular Parkinson's syndrome, Parkinson's symptoms accompanied by Alzheimer's disease, and Parkinson's symptoms accompanied by essential tremor, there may be cases of tremor and bradykinesia similar to Parkinson's symptoms, but it can be confirmed that dopamine neurons are normal. In the case of Parkinson's symptoms, it is important to distinguish Parkinson's disease from the diseases similar to Parkinson's disease. Brain magnetic resonance imaging (MRI) test is the first thing required to distinguish Parkinson's disease from secondary Parkinson's syndrome and atypical Parkinson's syndrome. MRI findings are normal in the case of Parkinson's disease, while other diseases show characteristic MRI findings. Internal disease causes systemic weakness, which is sometimes mistaken for Parkinson's syndrome. Among Parkinson's disease diagnosis methods, the internal disease test (blood test, urine test, electrocardiogram, chest X-ray test) is a test to confirm that there are no other internal diseases to confirm this.

However, the Parkinson's disease diagnosis methods described above are expensive and the diagnostic procedure is complicated. Lundbeck, one of the companies focusing on the treatment and diagnosis of Parkinson's disease, mentions the importance of developing tools for rapid diagnosis of Parkinson's disease on its website, but commercially available reagents or kits are currently not on sale. In addition, the number of patients suffering from Parkinson's disease is increasing year by year and the therapeutic drug market is growing significantly in proportion to this. However, the development of the market for Parkinson's disease diagnostic reagents has been insufficient. Therefore, it is an urgent request to develop a technology capable of quickly and economically diagnosing Parkinson's disease from its similar disease and concurrently performing the treatment.

The present inventors confirmed that the expression of DUSP10 mRNA is decreased in patients with Parkinson's disease, and the STT compound selected by docking simulation binds to the TPP domain of DUSP10. In addition, the present inventors confirmed that the STT compound inhibits ROS production in the Parkinson's disease cell model, exhibits neuronal cell protective activity through inhibition of apoptosis, and also protects dopamine neurons in the MPTP animal model and restores motility. Further, the present inventors have completed this invention by revealing that the compound can be used for the prevention and treatment of Parkinson's disease.

SUMMARY OF THE INVENTION

It is an object of the present invention to provide a pharmaceutical composition comprising a STT compound as an active ingredient for the prevention or treatment of Parkinson's disease.

To achieve the above object, the present invention provides a pharmaceutical composition comprising a STT compound as an active ingredient for the prevention or treatment of Parkinson's disease.

The present invention also provides a health functional food comprising STT (2-(5-Methyl-4-oxo-2-thioxo-1,3-thiazolidin-3-yl) ethanesulfonic acid) as an active ingredient for the prevention or amelioration of Parkinson's disease.

The present invention also provides a pharmaceutical composition comprising a DUSP10 protein or a polynucleotide encoding the same for the prevention or treatment of Parkinson's disease.

The present invention also provides a diagnostic composition for Parkinson's disease comprising a detection reagent that specifically binds to a DUSP10 protein or a polynucleotide encoding the same.

In addition, the present invention provides a method for providing Parkinson's disease diagnostic information comprising the steps of measuring the expression level of the DUSP10 protein or the polynucleotide encoding the same in a sample; and comparing the expression level with the protein expression level of a normal subject.

ADVANTAGEOUS EFFECT

The present inventors confirmed that the expression of DUSP10 mRNA was decreased in the blood and brain samples (Substantia Nigara) of Parkinson's disease patients and in vitro Parkinson's disease cell model, and the STT compound selected by docking simulation conjugated to the TPP domain of DUSP10. The STT compound inhibited ROS production and showed neuronal cell protective activity through inhibition of apoptosis in the Parkinson's disease cell model, and protected dopamine neurons and restored motility in the MPTP animal model, so it can be used for the prevention and treatment of Parkinson's disease.

BRIEF DESCRIPTION OF THE DRAWINGS

FIG. 1A: results using blood samples, and FIG. 1B: results using brain samples.

FIG. 5 is a diagram showing the DPSP (Druggable Pocket Site Prediction) equation for defining DPSP score for selecting a candidate ligand.

DESCRIPTION OF THE PREFERRED EMBODIMENTS

Figure 1A:
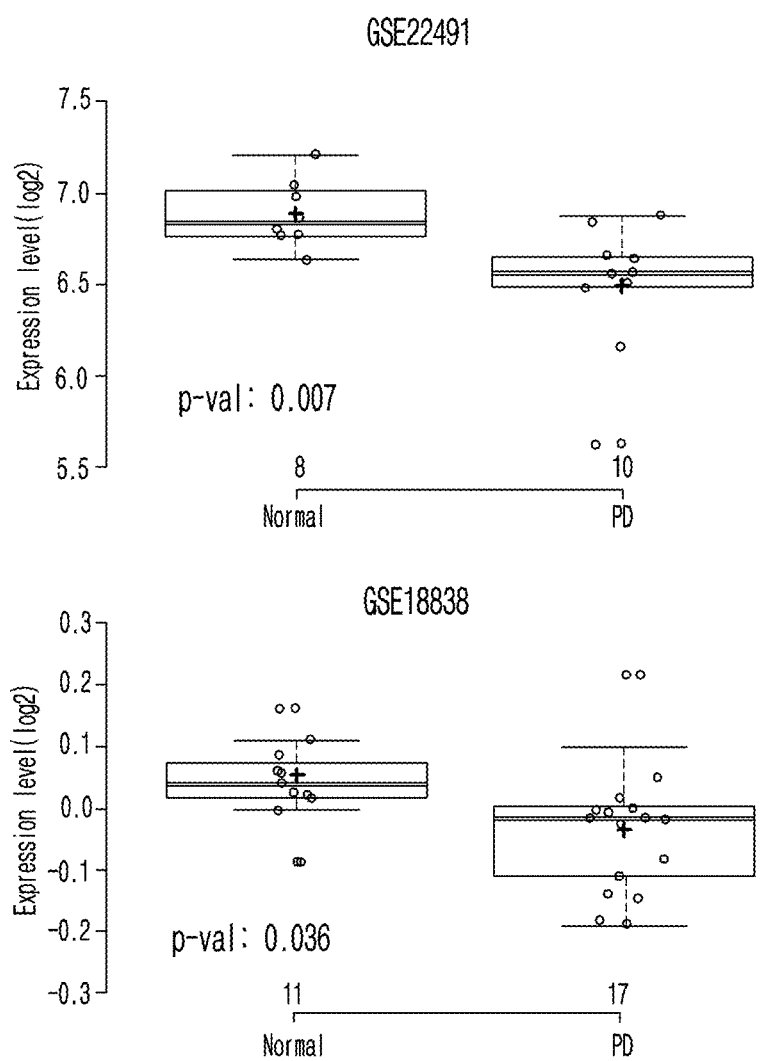
FIGS. 1A-1B are diagrams showing the difference in the expression level of DUSP10 mRNA confirmed in Parkinson's disease patients and normal people.

Hereinafter, the present invention is described in detail.

The present invention provides a pharmaceutical composition comprising STT (2-(5-Methyl-4-oxo-2-thioxo-1,3-thiazolidin-3-yl) ethanesulfonic acid) as an active ingredient for the prevention or treatment of Parkinson's disease.

The STT (2-(5-Methyl-4-oxo-2-thioxo-1,3-thiazolidin-3-yl) ethanesulfonic acid) has the structure of formula 1 below.

[Formula 1]

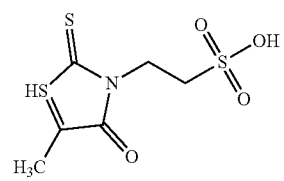

In the present invention, the STT can interact with the TPP domain of DUSP10.

In the present invention, the STT can suppress the ROS production.

The present invention also provides a pharmaceutical composition comprising a DUSP10 protein or a polynucleotide encoding the same as an active ingredient for the prevention or treatment of Parkinson's disease.

The DUSP10 protein can be a polypeptide composed of any sequence known in the art. The polypeptide can be a variant of amino acids having a different sequence by deletion, insertion, substitution or a combination thereof of amino acid residues, within a range that does not affect the function of the protein. Amino acid exchange in proteins or peptides that do not alter the activity of the molecule as a whole is known in the art. In some cases, it can be modified by phosphorylation, sulfation, acrylation, glycosylation, methylation, farnesylation, etc. Therefore, the present invention can include a polypeptide having an amino acid sequence substantially identical to the above polypeptide. The said substantially identical polypeptide can have homology with at least 80%, specifically at least 90% and more specifically at least 95% with the polypeptide of the present invention.

In addition, the polynucleotide encoding the DUSP10 protein can be a polynucleotide composed of any sequence known in the art. The present invention can include a polynucleotide having a nucleotide sequence substantially identical to the above polynucleotide or a fragment thereof. The said polynucleotide having the substantially identical nucleotide sequence can have homology with at least 80%, specifically at least 90% and more specifically at least 95% with the polynucleotide of the present invention.

The pharmaceutical composition of the present invention can include a carrier, a diluent, an excipient or a mixture thereof, generally used in biological agents. The pharmaceutically acceptable carrier can be any carrier that is able to deliver the composition into the human body without limitation, which is exemplified by the compounds described in Merck Index, 13th ed., Merck & Co. Inc., such as saline, sterilized water, Ringer's solution, dextrose solution, maltodextrin solution, glycerol, ethanol or a mixture thereof. If necessary, a general additive such as antioxidant, buffer, and bacteriostatic agent can be additionally added.

The composition of the present invention can be prepared by mixing with generally used diluents or excipients such as fillers, extenders, binders, wetting agents, disintegrating agents and surfactants.

The composition of the present invention can be formulated as an oral preparation or a parenteral preparation. The oral preparation can include solid and liquid formulations. The solid formulation can be tablets, pills, powders, granules, capsules or troches, and the solid formulation can be prepared by adding at least one excipient to the composition. The excipient can be starch, calcium carbonate, sucrose, lactose, gelatin or a mixture thereof. The solid formulation can include lubricants, which are exemplified with magnesium stearate and talc. Meanwhile, the liquid formulation can be suspensions, solutions, emulsions or syrups. At this time, the liquid formulation can include excipients such as wetting agents, sweeteners, fragrances and preservatives.

The parenteral preparation can include injections, suppositories, respiratory inhalation powders, spray aerosols, powders and creams. The injection can include sterilized aqueous solutions, non-aqueous solvents, suspensions, emulsions, and the like. The non-aqueous solvents and suspensions can contain propylene glycol, polyethylene glycol, vegetable oil like olive oil, and injectable ester like ethylolate, etc.

The composition of the present invention can be administered orally or parenterally according to the desired method. The parenteral administration can include intraperitoneal injection, rectal injection, subcutaneous injection, intravenous injection, intramuscular injection or intrathoracic injection.

The composition of the present invention is administered in a pharmaceutically effective dose. The effective dose can vary depending on the type of disease, the severity, the activity of the drug, the sensitivity to the drug, the route of administration, the time of administration and the rate of release, the duration of treatment, the drug being used concurrently, and the like. However, for the desired effect, the amount of the active ingredient contained in the pharmaceutical composition according to the present invention can be 0.0001~100 mg/kg, and specifically 0.001~10 mg/kg. The composition of the present invention can be administered once or several times a day.

The composition of the present invention can be administered alone or in combination with other therapeutic agents. In combination administration, the administration can be sequential or simultaneous.

Figure 7:
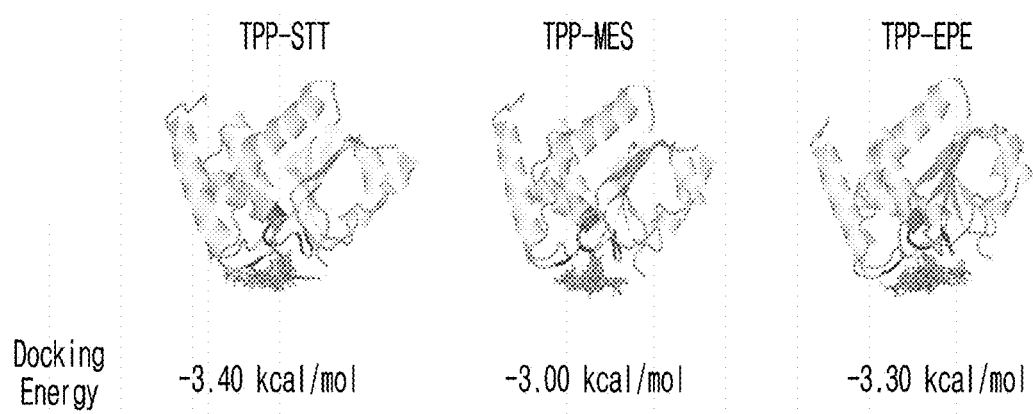
FIG. 7 is a diagram showing the molecular photos of STT, MES and EPE bound to TPP (tyrosinase protein phosphatase) and the docking energy of the same.
Figure 8A:
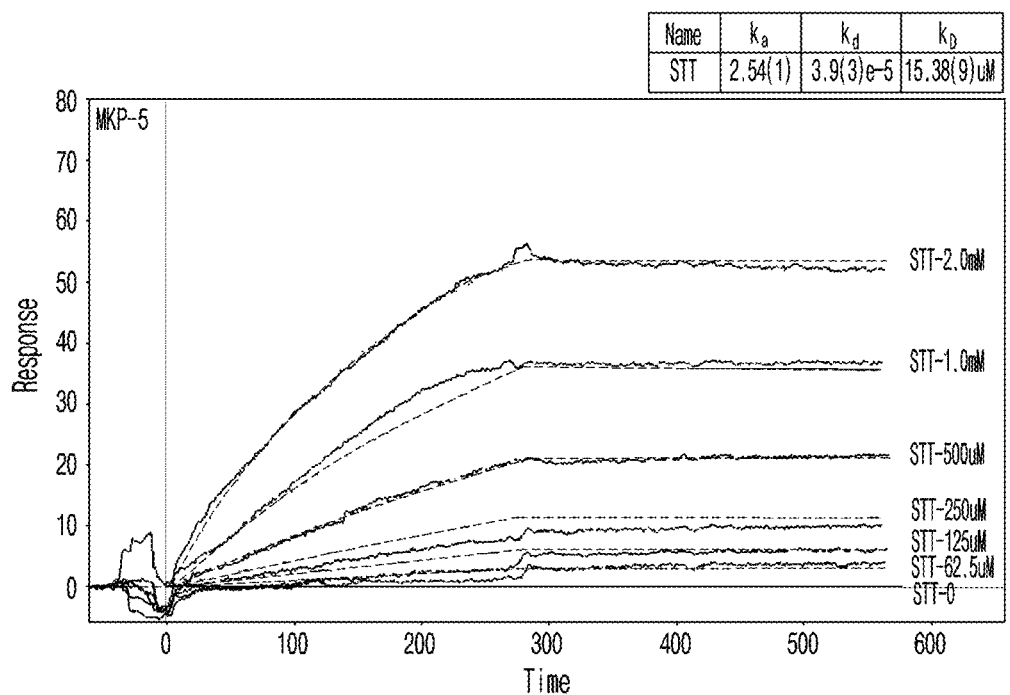
FIG. 8A is a diagram showing the results of SPR (Surface Plasmon Resonance) using STT.
Figure 8B:
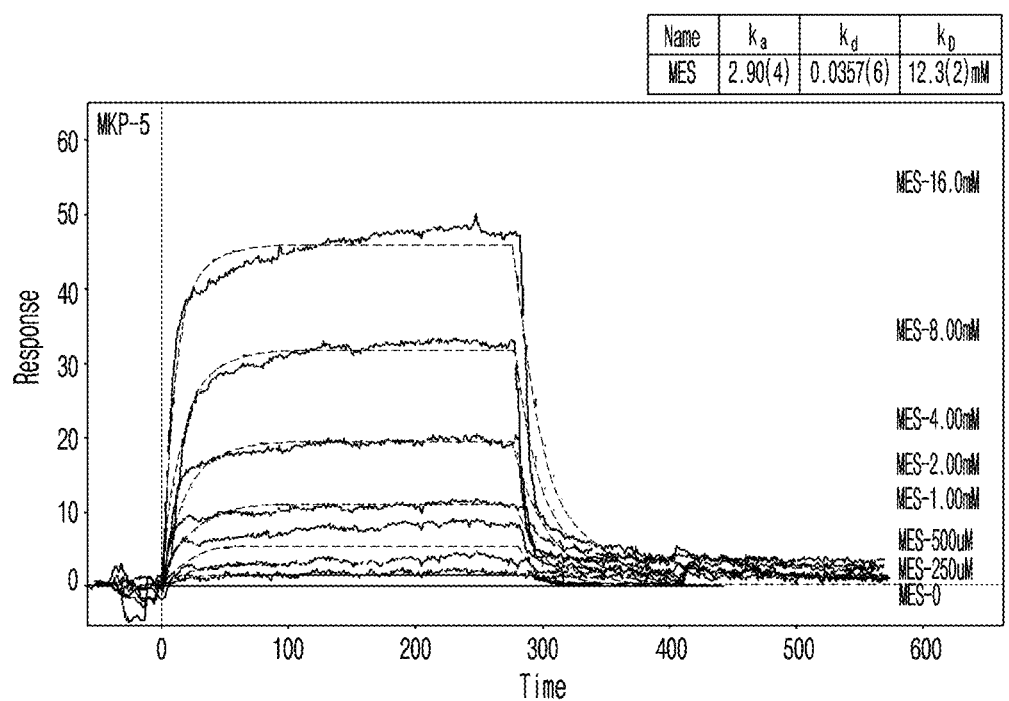
FIG. 8B is a diagram showing the results of SPR (Surface Plasmon Resonance) using MES.

In a preferred embodiment of the present invention, the present inventors performed docking simulation of the ligands selected through ligand screening and the DUSP10 protein to confirm that the STT was interacted strongly with the DUSP10 protein (see FIGS. 7, 8A and 8B). The present inventors also confirmed that the ROS production in the Parkinson's disease cell model was suppressed by the treatment of STT, and the neuroprotective activity was shown through the inhibition of apoptosis (see FIGS. 11~14). In addition, it was confirmed that the STT protected dopamine neurons in the MPTP animal model and restored motility (see FIGS. 15 and 16). Therefore, it was confirmed that the STT compound of the present invention can be effectively used for the prevention or treatment of Parkinson's disease.

The present invention also provides a health functional food comprising STT (2-(5-Methyl-4-oxo-2-thioxo-1,3-thiazolidin-3-yl) ethanesulfonic acid) as an active ingredient for the prevention or amelioration of Parkinson's disease.

The "health functional food" herein refers to a food prepared by using nutrients or ingredients having the functions useful for the human body that are easily deficient in everyday meals, and a food that helps health maintenance, but not always limited thereto. It includes all the conventional health foods.

The form and type of the health functional food are not particularly limited. Specifically, the health functional food can be in the form of tablets, capsules, powders, granules, liquids and pills. The health functional food can include various flavors, sweeteners or natural carbohydrates as additional ingredients. The sweeteners can be natural or synthetic sweeteners, and the natural sweeteners are exemplified by taumartin, stevia extract, and the like. The synthetic sweeteners are exemplified by saccharin and aspartame, etc. In addition, the natural carbohydrates can be monosaccharides, disaccharides, polysaccharides, oligosaccharides and sugar alcohols, etc.

In addition to the ingredients mentioned above, the health functional food of the present invention can include in a variety of nutrients, vitamins, minerals, flavors, coloring agents, pectic acid and its salts, alginic acid and its salts, organic acids, protective colloidal viscosifiers, pH regulators, stabilizers, antiseptics, glycerin, alcohols, etc. All the mentioned ingredients can be added singly or together. The proportion of those ingredients can be 0.01~0.1 weight part per 100 weight part of the composition of the present invention.

The STT (2-(5-Methyl-4-oxo-2-thioxo-1,3-thiazolidin-3-yl) ethanesulfonic acid) compound of the present invention can be added as it is or as mixed with other food components according to the conventional method. The mixing ratio of active ingredients can be regulated according to the purpose of use. In general, the content in the health functional food can be 0.01~90 weight part by the total food weight. However, if long term administration is required for health and hygiene or regulating health condition, the content can be lower than the above but higher content can be accepted as well since the STT compound of the present invention has been proved to be very safe.

The present invention also provides a diagnostic composition for Parkinson's disease comprising a detection reagent that specifically binds to a DUSP10 protein or a polynucleotide encoding the same.

According to an embodiment of the present invention, Parkinson's disease can be diagnosed by measuring the amount of DUSP10 protein or the expression level of the gene encoding the same, which is significantly reduced in Parkinson's disease patients compared to healthy normal people.

The DUSP10 protein can be a polypeptide composed of any sequence known in the art. Particularly, the DUSP10 protein can be a polypeptide consisting of SEQ. ID. NO: 1.

The polypeptide can be modified by phosphorylation, sulfation, acrylation, glycosylation, methylation or farnesylation.

In addition, the polynucleotide encoding the DUSP10 protein can be a polynucleotide composed of any sequence known in the art. Particularly, the polynucleotide encoding the DUSP10 protein can be a polynucleotide consisting of SEQ. ID. NO: 2.

The polynucleotide of the present invention can include a variant in which one or more nucleotide sequences are substituted, deleted or inserted as long as it encodes a protein having equivalent activity.

The detection reagent in the composition according to the present invention can be any one or more selected from the group consisting of antibodies, antibody fragments, aptamers, primers, probes and anti-sense nucleotides. When DUSP10 protein is to be detected, the detection reagent can be any one or more selected from the group consisting of antibodies, antibody fragments and aptamers. In the case of the polynucleotide encoding DUSP10 protein, the detection reagent can be any one or more selected from the group consisting of primers, probes and antisense nucleotides.

The antibody can be a monoclonal antibody, polyclonal antibody or recombinant antibody. The antibody can be easily prepared using the techniques well known in the art. The antibody fragment can include a functional fragment of an antibody molecule. The functional fragment of an antibody molecule refers to a fragment having at least antigen binding function and can be Fab, F(ab'), F(ab')2 and Fv, and the like. The aptamer is an oligonucleotide molecule having binding activity to a target molecule, and can be RNA, DNA, modified oligonucleotide or a mixture thereof, and can be in linear or cyclic form.

The monoclonal antibody can be prepared using hybridoma technique or phage antibody library technique well known in the art. In general, the hybridoma cells secreting monoclonal antibodies can be prepared by fusing cancer cells with immune cells isolated from immunologically suitable host animals, such as mice injected with antigenic proteins. The cell fusion of such two groups can be performed using the methods known in the art, such as using polyethylene glycol, and the cells producing antibodies can be proliferated by the standard culture methods. Specifically, subcloning can be performed using a limiting dilution method to obtain a uniform cell population, and then the hybridoma cells capable of producing an antibody specific to the antigen can be prepared by mass-culturing in vitro or in vivo. The antibodies prepared by the method above can be isolated and purified using the methods such as gel electrophoresis, dialysis, salt precipitation, ion exchange chromatography, affinity chromatography, etc.

The polyclonal antibody can be prepared by injecting a biomarker protein or a fragment thereof, an immunogen, into an external host according to the methods well known in the art. The external host can be a mammal such as a mouse, a rat, a sheep, and a rabbit. When the immunogen is injected by intramuscular, intraperitoneal or subcutaneous injection, it can be administered with an adjuvant to increase antigenicity. Then, blood is periodically collected from the external host to obtain the serum showing improved titer and antigen specificity, from which the antibody can be isolated and purified.

The primer is complementary to the polynucleotide encoding the DUSP10 protein of the present invention, and any primer designed to amplify thereof can be used.

The probe is a nucleic acid fragment corresponding to a few to several hundred nucleotides specifically binding with DNA or RNA, which can be used to confirm the presence or absence of specific DNA or RNA. The probe can be prepared in the form of an oligonucleotide probe, a single-stranded DNA probe, a double-stranded DNA probe, a RNA probe, etc., and can be labeled with biotin, FITC, rhodamine, DIG (digoxigenin) or radioisotope.

The antisense nucleotide can have double or single-stranded DNA, double or single-stranded RNA, DNA/RNA hybrid, DNA and RNA analogs and nucleotides, sugar or backbone modifications.

The detection reagent can further include a ligand that can specifically bind to the detection reagent. The ligand can be a conjugate labeled with a detector such as a chromogenic enzyme, a fluorescent material, a radioisotope or a colloid, and a ligand treated with streptavidin or avidin.

In addition to the detection reagent described above, the diagnostic composition for Parkinson's disease can include distilled water or a buffer to stably maintain the structure thereof.

In addition, the present invention provides a method for providing Parkinson's disease diagnostic information comprising the steps of measuring the expression level of the DUSP10 protein or the polynucleotide encoding the same in a biological sample; and comparing the expression level with that of a normal subject.

In a preferred embodiment of the present invention, it was confirmed that the expression level of DUSP10 mRNA was reduced in the tissue of Parkinson's disease patients compared to that of the negative control group. Therefore, it is possible to provide Parkinson's disease diagnostic information through the comparative analysis of the expression level of the DUSP10 protein or the polynucleotide encoding the same in a biological sample.

The sample can include a biosample capable of identifying a disease-specific polypeptide that can be distinguished from a normal state such as urine, blood, serum or plasma.

The sample can be pretreated using anion exchange chromatography, affinity chromatography, size exclusion chromatography, liquid chromatography, continuous extraction, centrifugation or gel electrophoresis.

The expression level of DUSP10 protein can be measured by any one or more methods selected from the group consisting of enzyme-linked immunosorbent assay (ELISA), radioimmunoassay, sandwich enzyme immunoassay, Western blotting, immunoprecipitation, immunohistochemistry and fluoroimmunoassay.

The expression level of the polynucleotide encoding the DUSP10 protein can be measured by any one or more methods selected from the group consisting of reverse transcription polymerase chain reaction (RT-PCR), competitive RT-PCR, real-time RT-PCR, RNase protection assay, Northern blotting and microarray.

The control group is healthy people without Parkinson's disease. Therefore, in the method of the present invention, when the expression level of DUSP10 protein or the expression level of the polynucleotide encoding the same is lower than that of the control group (normal group), it can be determined that Parkinson's disease has already developed or has a high risk of developing.

Hereinafter, the present invention will be described in detail by the following examples.

However, the following examples are only for illustrating the present invention, and the contents of the present invention are not limited thereto.

EXPERIMENTAL EXAMPLE 1

Confirmation of DUSP10 Expression Difference Between Parkinson's Disease Patients and Normal People Parkinson's disease patient blood and neuron gene expression data sets were collected from the GEO (Gene Expression Omnibus) database, an open online transcript database. After normalizing the expression levels of individual genes and other precursors (approximately 50,000) from the collected data, DUSP10 was identified as a differentially expressed gene (DEG) between the normal group and the Parkinson's disease patient group. In addition, T test was performed for statistical analysis to identify the patient group in which the DUSP10 mRNA expression level was statistically/significantly different from that of the normal group.

Figure 1B:
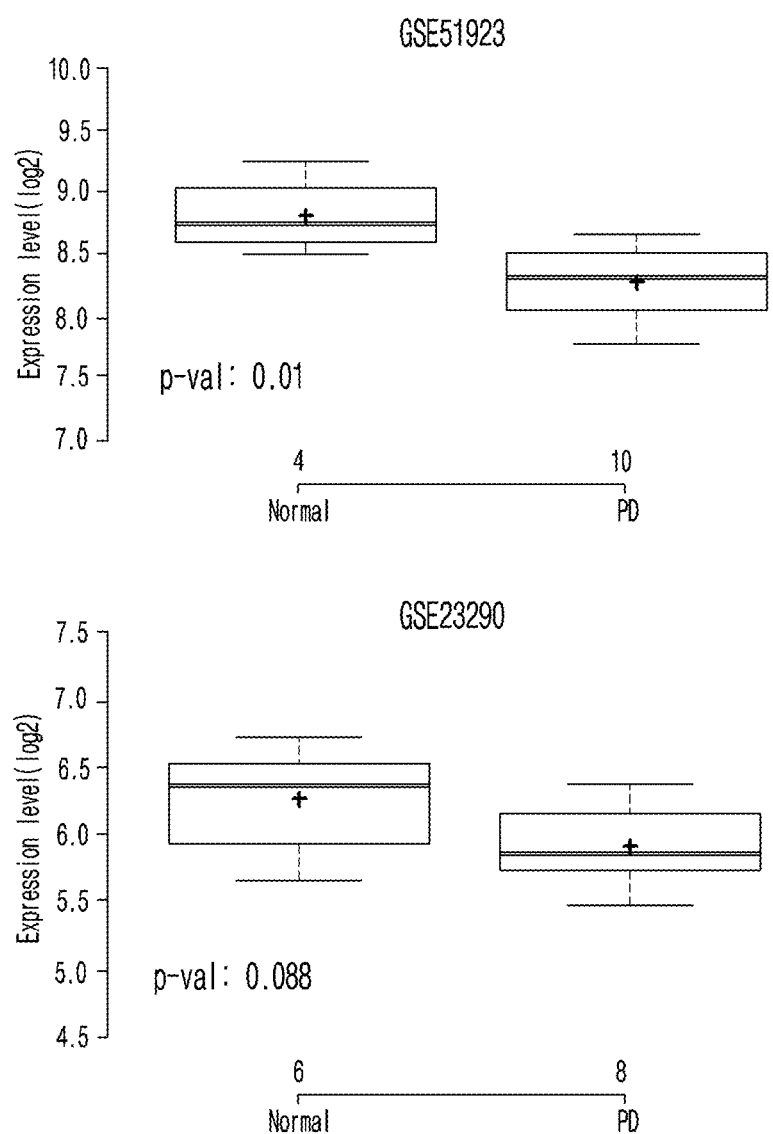
Figure 2:
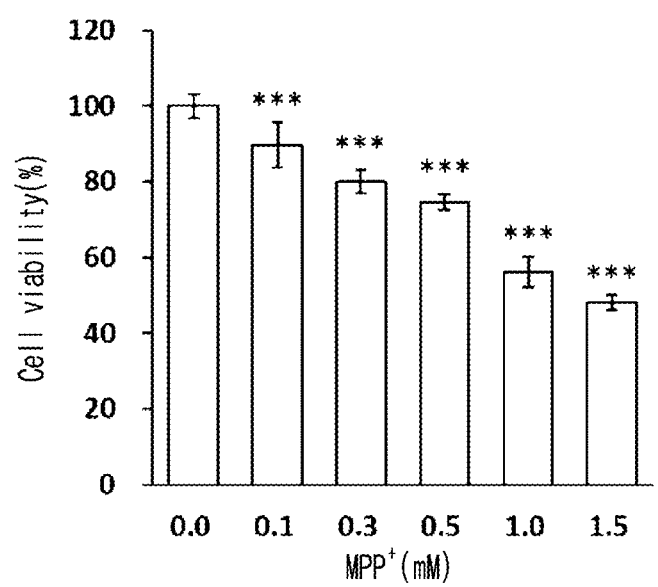
FIG. 2 is a diagram showing the cell viability after treating SH-SY5Y cells with MPP+ at various concentrations for 24 hours.
Figure 3:
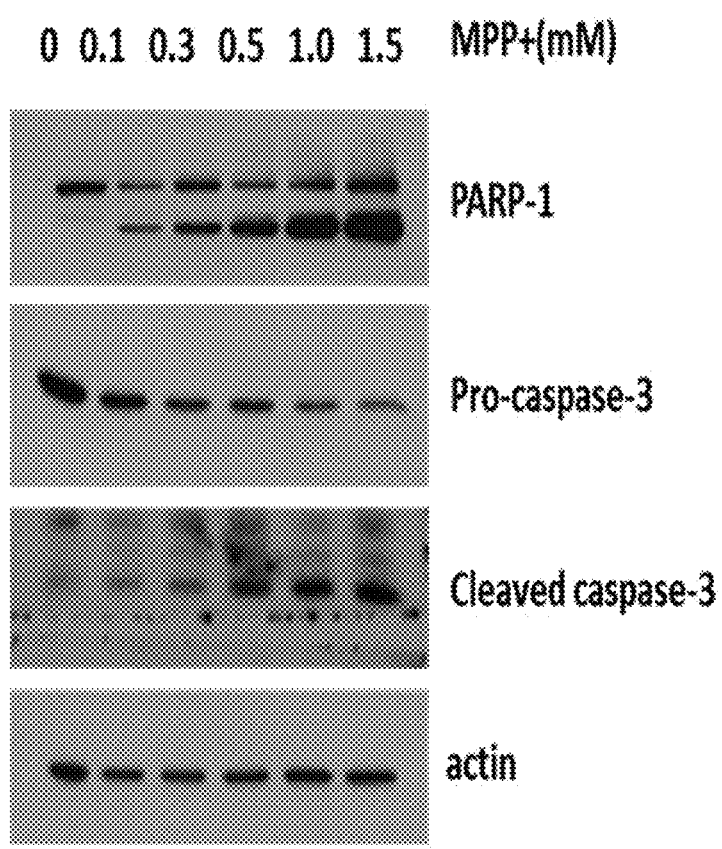
FIG. 3 is a diagram showing the degree of cleavage of PARP-1 according to the treatment of MPP+ in the Parkinson's disease cell model.

The number starting with GSE in FIGS. 1A and 1B is a unique number of the GEO (Gene Expression Omnibus) database, which is an online transcript database. GSE22491 and GSE18838 are data sets that measured the gene expression from blood, and GSE51923 and GSE23290 are data sets that measured the gene expression from neurons. FIG. 1A shows the difference in the DUSP10 mRNA expression level between the normal control group and the Parkinson's disease patients in the blood derived gene expression data sets (GSE22491 and GSE18838), and the expression level is expressed in log 2. FIG. 1B shows the difference in the DUSP10 mRNA expression level between the normal control group and the Parkinson's disease patients in the neuron derived gene expression data sets (GSE51923 and GSE23290), and the expression level is expressed in log 2. In the blood and neurons, the DUSP10 mRNA expression level in Parkinson's disease patients was lower than that of the normal people, and was statistically significant (FIGS. 1A and 1B).

EXPERIMENTAL EXAMPLE 2

Confirmation of Changes of DUSP10 Expression in PD Cell Model Using MPP+

Human neuroblastoma SH-SY5Y cells were cultured in DMEM (Wellgene, Korea) supplemented with 10% FBS (Cellgro, Va., USA) and antibiotics in the condition of 5% $CO_2$ at 37° C., to which MPP+ was treated at the various concentrations. Twenty four hours later, the cells were obtained, and the whole protein was extracted using NP-40 lysis buffer. The protein was quantified, separated by SDS-PAGE and transferred to a polyvinylidene difluoride (PVDF) membrane. Then, blocking was performed using 5% skim milk at 4° C. overnight. The primary antibody of each protein shown in FIG. 4 was diluted (1:2000) and then treated to the membrane at room temperature for 2 hours, and the HRP-conjugated secondary antibody was diluted (1:10,000) and then treated to the membrane at room temperature for 1 hour. And it was printed on x-ray film using ECL solution.

Figure 4:
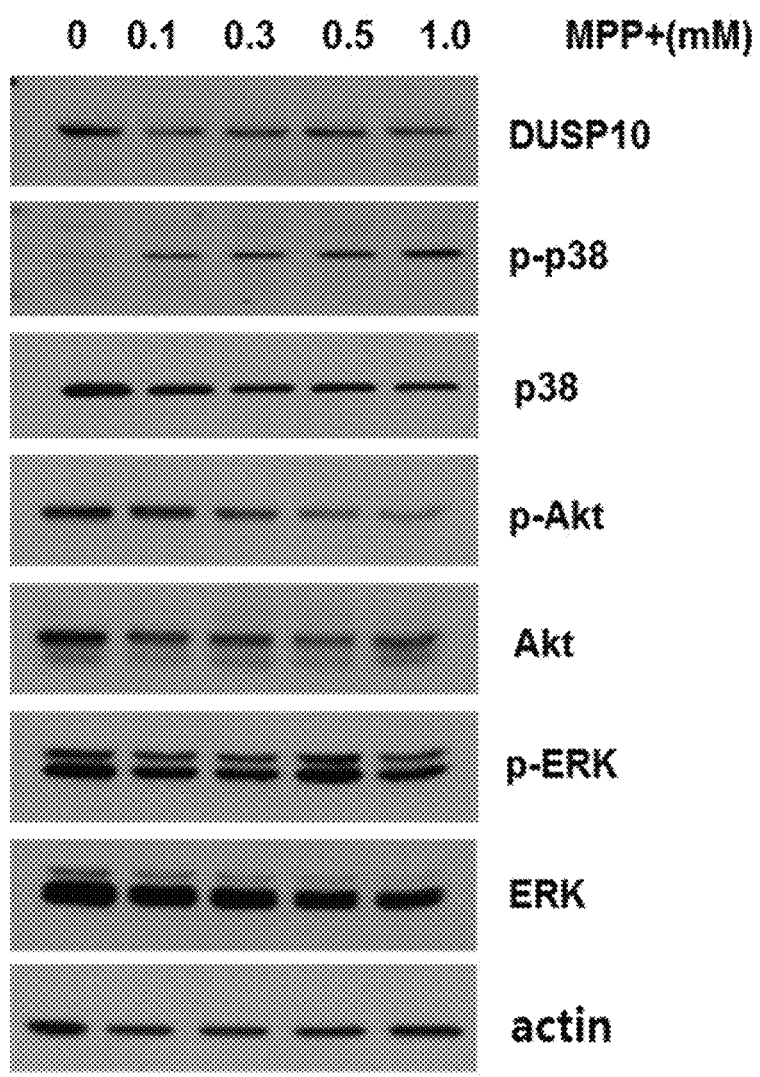
FIG. 4 is a diagram showing the expression pattern of various proteins including DUSP10 according to the treatment of MPP+ in the Parkinson's disease cell model.

As a result, when SH-SY5Y cells were treated with MPP+, the phosphorylation of p38, an apoptotic factor, was increased and the phosphorylation Akt, a cell survival factor, was decreased as the concentration of MPP+ was increased. In addition, it was confirmed that the expression of DUSP10 was reduced under the same conditions above (FIG. 4). The above results suggest that the apoptotic signal was activated by suppressing the dephosphorylation of p38, an apoptotic factor, DUSP10-dependently.

EXPERIMENTAL EXAMPLE 3

Ligand Screening and Docking Simulation

The catalytic domain of human MAP kinase phosphatase 5 (PDB ID: 1ZZW) was selected as a target protein involved in DUSP10 gene. 1ZZW has a nucleotide sequence composed of 149 amino acids and contains tyrosine-protein phosphatase domain (TPP domain), the active part responsible for the phosphorylation of DUSP10 protein. This methodology predicts the binding site of the target protein from the similar known structures and pockets of the target protein based on the accumulated data. First, the HHblits program was used to find the similar structures using local sequence alignment, and their ligand binding site information was collected (Remmert, M., Biegert, A., Hauser, A. and Soding, J. (2011) HHblits: lightning-fast iterative protein sequence searching by HMM-HMM alignment. *Nat Methods*, 9, 173-175).

Figure 6:
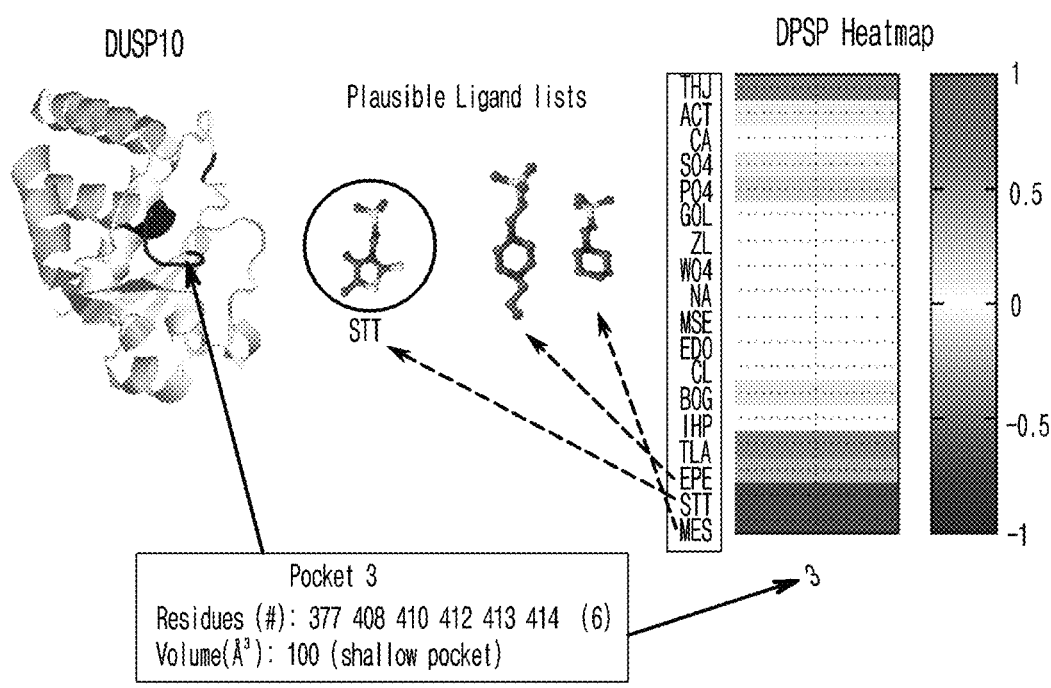
FIG. 6 is a diagram showing the actual application of DPSP to screen active ligands for DUSP10, and the three compounds (STT, MES and EPE) that can be bound to the pocket 3 of DUSP10 among the various ligands extracted from the database through DPSP heatmap.

Then, the geometry pocket formed in the target protein was measured using Pck module of VMD program (schwarz.benjamin.free.fr/Work/Pck/home.htm). Ligand binding information of the similar structures was mapped on the pocket site of the target protein and the most possible ligand binding site was selected based on the scoring function (D-score). D-score is the sum of 9 scores considering the characteristics of the target and similar structures, and the higher the score, the higher the probability of ligand binding in the target protein (FIG. 7). The most possible binding sites in the 1ZZW structure were determined by V354, T355, L373, A375, T376, D377, L383, H407, C408, Q409, A410, G411, V412, 5413, R414, 5415 and 1418. These pockets seem to be well predicted by the presence of the PO4 (phosphate ion) ligand present in the 1ZZW produced as a result of the phosphorylation. In these pockets, 32 of the 41 predicted ligands were involved. In order to investigate the 32 ligands (2WT, 3LU, 4NP, 5P5, 79W, ACT, ACY, B2B, CL, CSN, DVG, EDO, EPE, FLC, FMT, GLC, IHS, JZG, MES, MLT, NO3, PDV, PEG, PO4, PSY, PTR, PVS, SO4, STT, VO4, WO4 and YI1) in detail, and to select a ligand that can be used as a new drug among the 32 ligands, Lipinski's 5 rules (R05) were applied. Lipinski's RO5 defines the five characteristics of a new drug candidate: molecular weight less than 500 Daltons, LogP less than 5, hydrogen bond donors less than 5, hydrogen bond receptors less than 10, and molar refractiveness between 40 and 130. RO5 of the 32 ligands was calculated in PDB (Protein Data Bank). As a result, 10 out of the 32 ligands satisfying RO5 are presented in FIGS. 8A and 8B. The present inventors also selected the top three compounds (MES, STT and EPE) that could be synthesized by sorting the D-stores according to high score order for testing in vitro and in vivo (FIG. 6).

Docking simulation of the 3 selected compounds and DUSP10 protein was performed. Autodock-Vina program was used for the docking simulation (FIG. 7). [Reference] O. Trott, A. J. Olson, AutoDock Vina: improving the speed and accuracy of docking with a new scoring function, efficient optimization and multithreading, Journal of Computational Chemistry 31 (2010) 455-461

As a result, it was confirmed that STT showed the most stable energy state and had the strongest interaction.

EXPERIMENTAL EXAMPLE 4

SPR Experiment with STT and MES

SPR (Surface Plasmon Resonance) assay was performed using Reichert SR7500DC system to confirm the presence or absence of interaction between the compounds above and the TPP domain of DUSP10. As a result, it was confirmed that STT had a relatively strong interaction with the TPP domain and MES had a weak interaction (FIGS. 8A and 8B, Tables 1 and 2, (Kd: dissociation rate; Ka: association rate; KD=Kd/Ka)).

TABLE 1

| Analyte | Running Buffer | Conc. | $K_a$ $[M^{-1}s^{-1}]$ | $K_d$ $[s^{-1}]$ | $K_D$ $[M]$ |
|---|---|---|---|---|---|
| MES(1) | 1xPBS, pH 7.4 | 0.25, 0.5, 1, 2, 4, 8, 16 mM | 3.50(5) | 0.0627(9) | 17.9(3) mM |
| MES(2) | 1xPBS, 2% DMSO | 0.25, 0.5, 1, 2, 4, 8, 16 mM | 2.90(4) | 0.0357(6) | 12.3(2) mM |
| EPE(1) | 1xPBS, pH 7.4 | 1, 2, 4, 8, 16 mM | — | — | — |
| EPE(2) | 1xPBS, 2% DMSO | 1, 2, 4, 8, 16 mM | — | — | — |
| STT(1) | 1xPBS, pH 7.4 | 0.125, 0.25, 0.5, 1, 2 mM | 1.70(6) | 4.6(5)e-5 | 26.9(9 μM |
| STT(2) | 1xPBS, 2% DMSO | 0.0625, 0.125, 0.25, 0.5, 1, 2 mM | 2.54(1) | 3.9(3)e-5 | 15.38(9) μM |

TABLE 2

| Analyte | Conc. | $K_a$ $[M^{-1}s^{-1}]$ | $K_a$ $[s^{-1}]$ | $K_D$ $[M]$ |
|---|---|---|---|---|
| MES(1-1) | 0, 3.125, 6.25, 12.5, 25, 50, 100, 200 mM | 0.152(7) | 0.0096(2) | 63(3) mM |
| STT(2) | 0, 0.625, 1.25, 2.5, 5, 10 mM | 0.4504 | 8.60e-5 | 190.922 uM |

EXPERIMENTAL EXAMPLE 5

Confirmation of STT Effect in PD Cell Model

<5-1> STT Cytotoxicity Test

Figure 9:
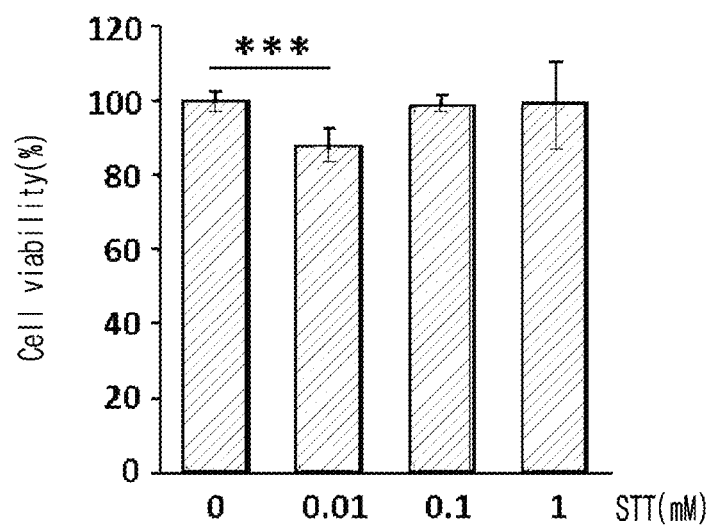
FIG. 9 is a diagram showing the cytotoxicity of STT in SH-SY5Y cells.

In order to investigate the cytotoxicity of STT predicted to bind to DUSP10, SH-SY5Y cells were prepared in 24-well plates as described in Experimental Example 2, and each concentration of STT was treated thereto for 24 hours. Then, 3-(4,5-dimethylthiazol-2-yl)-2,5-diphenyltetrazolium bromide (MTT) was treated to each well of the plate at the concentration of 0.1 mg/ml and cultured at 37° C. for 2 hours. The medium was removed and dimethyl sulfoxide (DMSO) was added thereto. Then, $OD_{540}$ was measured using an ELISA plate reader. As a result, it was confirmed that there was no cytotoxicity at the concentration (FIG. 9).

<5-2> Confirmation of Neuroprotective Effect of STT in PD Cell Model

Whether STT can inhibit apoptosis in the PD cell model was investigated. SH-SY5Y cells were prepared in 24-well plates as described in Experimental Example 2, and 0.5 mM MPP+ and 1 mM STT were treated thereto respectively or together for 24 hours. For MTT assay, MTT (Sigma, St Louis, Mo.) was added to each well of the plate at the concentration of 0.1 mg/ml and cultured at 37° C. for 2 hours. The medium was removed and dimethyl sulfoxide (DMSO) was added thereto. Then, $OD_{540}$ was measured using an ELISA plate reader (Bio-Tek Instruments Inc, Winooski, Vt.). All values were averaged in at least three wells through four independent experiments.

Figure 10:
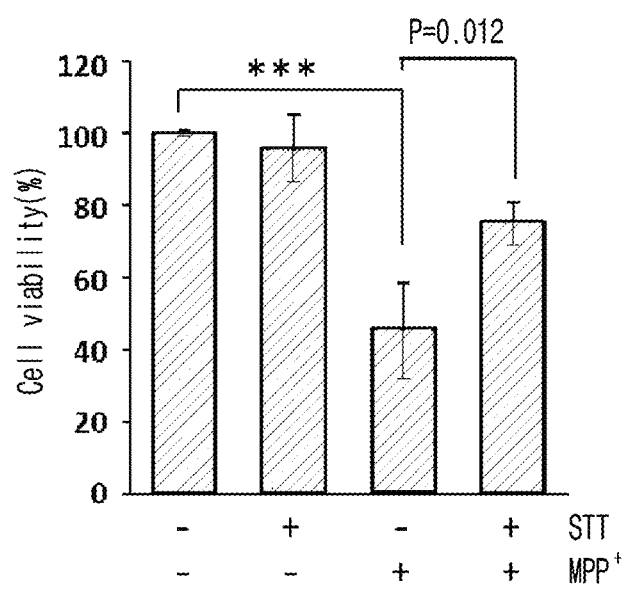
FIG. 10 is a diagram showing the neuroprotective effect of STT in the Parkinson's disease cell model, confirmed by MTT assay.

As a result, it was confirmed that the number of cells reduced by MPP+ was recovered by the treatment of STT (FIG. 10).

Figure 11:
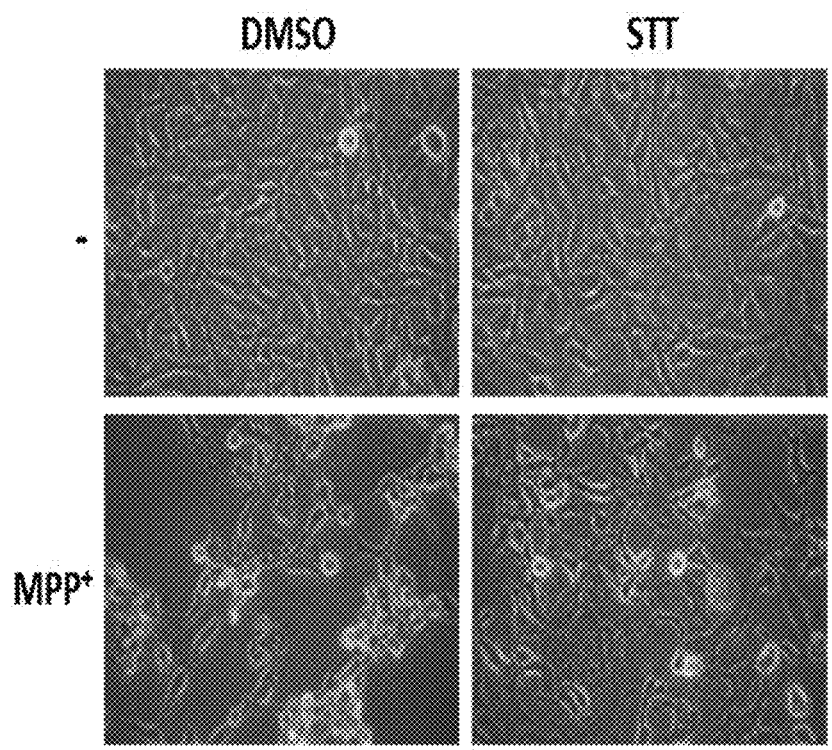
FIG. 11 is a diagram showing that the apoptosis caused by MPP+ is inhibited by STT in the Parkinson's disease cell model.

<5-3> Confirmation of Neuroprotective Effect of STT in PD Cell Model Using Microscope The cells treated with 0.5 mM MPP+ and 1 mM STT for 24 hours as described in <5-2>, were observed under a microscope. As a result, it was confirmed that the number of cells reduced by MPP+ was recovered by the treatment of STT (FIG. 11).

<5-4> Confirmation of Effect of STT on PARP Cleavage in PD Cell Model

Whether the STT treatment can suppress the apoptotic signals caused by MPP+ was investigated. Human neuroblastoma SH-SY5Y cells were cultured in DMEM (Wellgene, Korea) supplemented with 10% FBS (Cellgro, Va., USA) and antibiotics in the condition of 5% $CO_2$ at 37° C., to which 0.5 mM MPP+ and 1 mM STT were treated. Twenty four hours later, the cells were obtained, and the whole protein was extracted using NP-40 lysis buffer. The protein was quantified, separated by SDS-PAGE and transferred to a polyvinylidene difluoride (PVDF) membrane. Then, blocking was performed using 5% skim milk at 4° C. overnight. The primary antibody of each protein shown in FIG. 4 was diluted (1:2000) and then treated to the membrane at room temperature for 2 hours, and the HRP-conjugated secondary antibody was diluted (1:10,000) and then treated to the membrane at room temperature for 1 hour. And it was printed on x-ray film using ECL solution.

Figure 12:
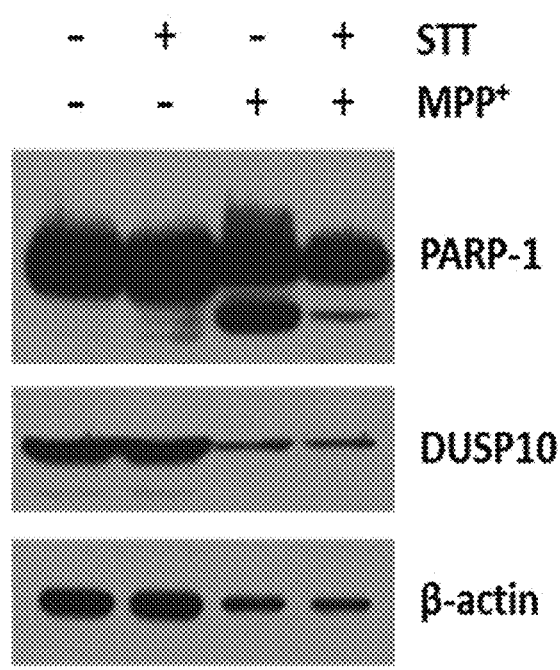
FIG. 12 is a diagram showing that the PARP-1 cleavage induced by MPP+ is inhibited by STT in the Parkinson's disease cell model.

As a result, it was confirmed that the PARP cleavage was reduced by the treatment of STT (FIG. 12).

<5-5> Confirmation of Effect of STT on ROS in PD Cell Model

MPP+ is known to induce ROS generation in cells and cause apoptosis. Therefore, whether STT can inhibit the ROS production induced by MPP+ was investigated.

Figure 13:
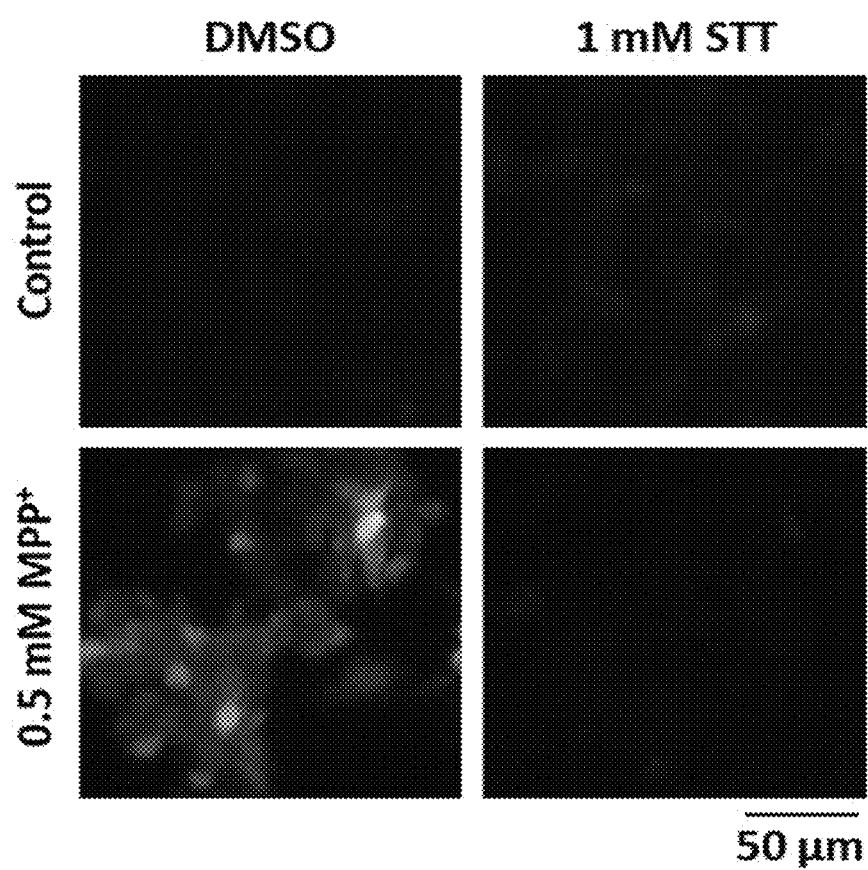
FIG. 13 is a diagram showing that the ROS production induced by MPP+ is reduced by STT in the Parkinson's disease cell model.
Figure 14:
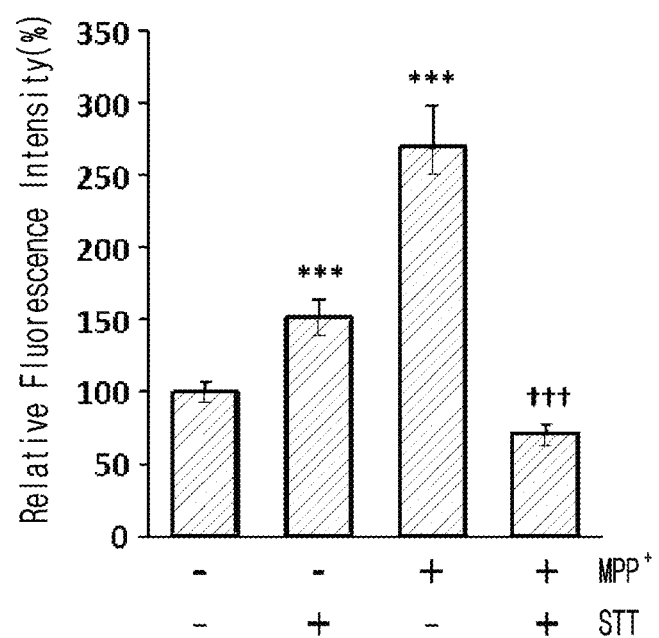
FIG. 14 is a diagram showing the results of quantifying the scores of FIG. 13 using image J program.
Figure 15:
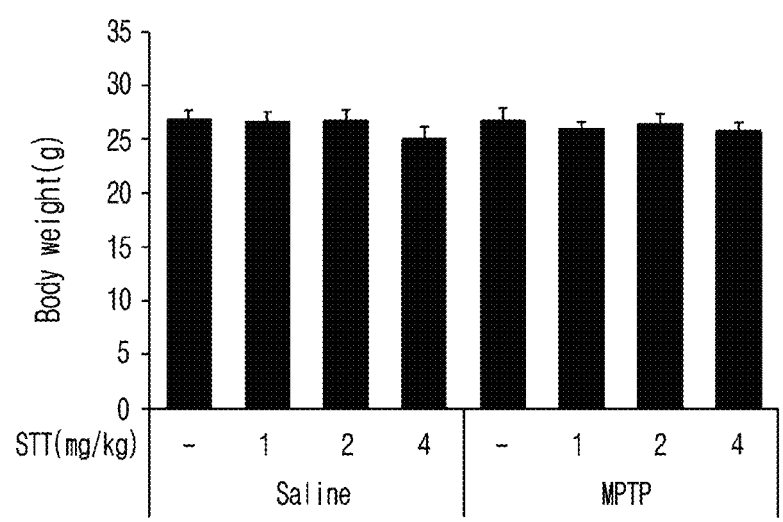
FIG. 15 is a diagram showing the changes in the body weight of the animal when STT is administered to the MPTP animal model.

Human neuroblastoma SH-SY5Y cells were cultured in DMEM (Wellgene, Korea) supplemented with 10% FBS (Cellgro, Va., USA) and antibiotics in the condition of 5% $CO_2$ at 37° C., to which 0.5 mM MPP+ and 1 mM STT were treated. DCFH-DA was treated thereto at 37° C. for 30 minutes, which was washed with PBS. Then, the degree of ROS production in the cells was observed under a fluorescence microscope. As a result, it was confirmed that the ROS increased by MPP+ was decreased by the treatment of STT (FIGS. 13 and 14).

EXPERIMENTAL EXAMPLE 6

Confirmation of STT Effect in MPTP Mouse Model

<6-1> Confirmation of Effect of STT on Motility Reduction Caused by Parkinson's Disease Male C57BL/6 mice (10 weeks old) were purchased from Daehan bio-link (Chungbuk, Korea). The mice were administered with 20 mg/kg of MPTP by intraperitoneal injection 4 times at 2 hour intervals (total 80 mg/kg), and sacrificed 7 days after the final injection. This experiment was performed in compliance with the Animal Experiment Guide edited by the Korean Academy of Medical Sciences.

To confirm the effect of the STT administration on the motility reduced by Parkinson's disease, a rotarod assay was performed. The mice were trained five times a day for two consecutive days until they could stay for 300 seconds on a rotating drum. The rotarod speed during the first training was constant at 10 rpm, and the rotarod speed was accelerated from 5 to 20 rpm for minutes during the second training. In the test session, the speed was increased from 5 to 40 rpm for 300 seconds. Each mouse was tested 5 times at 300 second intervals, and an average of 5 tests per test session was considered as the final score. The waiting time falling off the rotarod was automatically measured with an infrared sensor at 5 rpm of Rotamex (Columbus Inst, Columbus, Ohio).

Figure 16:
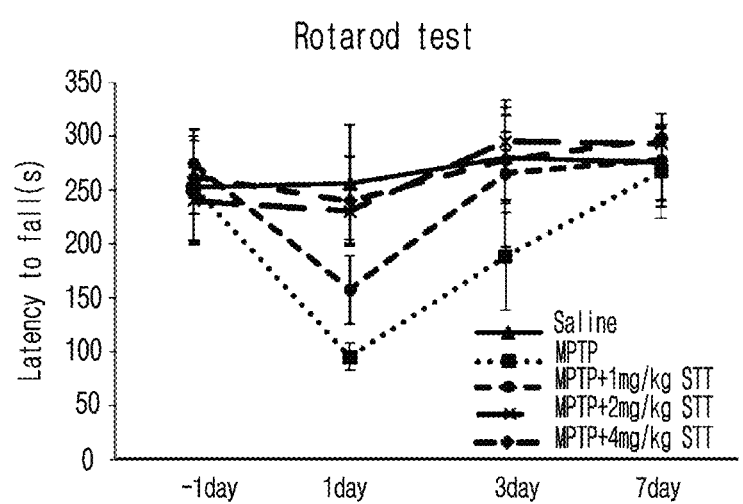
FIG. 16 is a diagram showing that the reduced motility of the MPTP animal model is significantly improved by the administration of STT.

As a result, it was confirmed that the motility of the mouse with Parkinson's disease induced by MPTP was significantly reduced, but the motility was restored by STT dose-dependently (FIG. 16).

<6-2> Confirmation of Effect of STT on Dopaminergic Neurons in MPTP Mouse Model (1)

In the corpus striatum of the brain, the fibers of dopaminergic neurons originating in the midbrain are stretching and working. To confirm the presence of dopaminergic neurons, cryosections of the rat brain tissue were prepared. Particularly, the rat brain fixed with 4% PFA was stored in a 30% sucrose solution for 1 day, and then frozen at −20° C. for 1 hour using an OCT compound. After preparing 20 μm-thick sections using a cyrosection device, histoimmunostaining was performed using an antibody to tyrosine hydroxylase (TH), a specific protein expressed in dopaminergic cells. To perform histoimmunostaining, the sections were washed with PBS, treated with 0.3% tritonX-100 (PBS) for 20 minutes at room temperature, and blocked with 5% FBS (PBS) solution for 1 hour at room temperature. Then, the sections were reacted with the TH antibody (1:2000) overnight at 4° C., washed with PBS, and reacted with the biotin-conjugated secondary antibody for 1 hour at room temperature and sequentially with the ABC elite solution (Vector Laboratories, Burlingame, Calif.) for 1 hour at room temperature. After coloring with DAB solution, the sections were treated with 70%, 80%, 90%, 95%, 100% ethanol and xylene for 5 minutes each, and then fixed on a slide and observed under a microscope.

Figure 17:
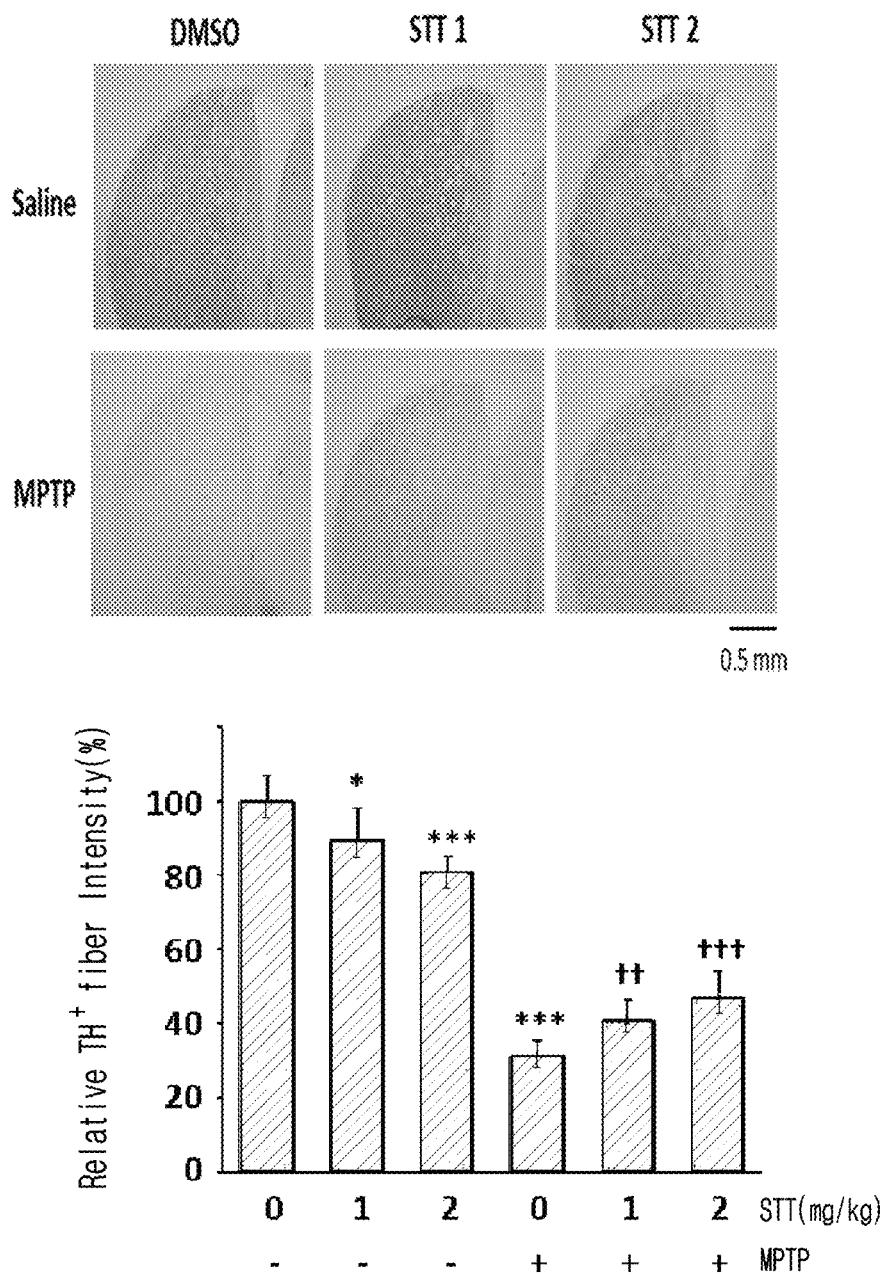
FIG. 17 is a diagram showing that the fibers of dopaminergic neurons reduced by MPTP are increased again by STT in the corpus striatum.

As a result, it was confirmed that the fibers of dopaminergic neurons in the corpus striatum reduced by MPTP were increased again by the administration of STT. The expression level of TH observed by histoimmunostaining was quantified using imageJ software (FIG. 17).

<6-3> Confirmation of Effect of STT on Dopaminergic Neurons in MPTP Mouse Model (2)

Figure 18:
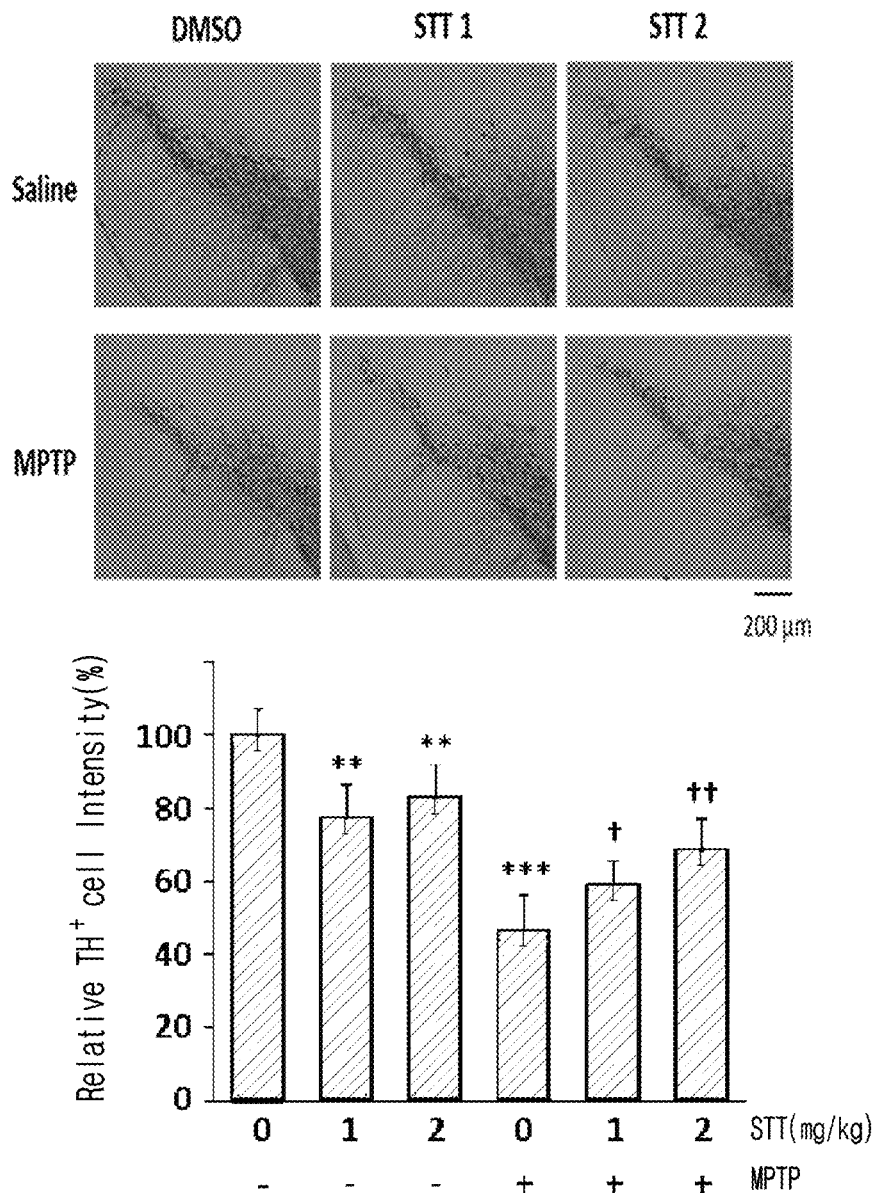
FIG. 18 is a diagram showing that the cell bodies of dopaminergic neurons reduced by MPTP are increased again by STT in the substantia nigra.

Histoimmunostaining for TH was performed in the same manner as described in <6-2> to confirm the distribution of the cell bodies of dopaminergic neurons in the substantia nigra of the midbrain. Then, the number of cells stained with the TH antibody was quantified and compared, and the results are shown in FIG. 18. As a result, it was confirmed that the cell bodies of dopaminergic neurons reduced by MPTP were recovered again by STT (FIG. 18).

What is claimed is:

1. A method for treating Parkinson's disease in a subject in need of treatment, the method comprising administering to the subject a composition comprising STT (2-(5-Methyl-4-oxo-2-thioxo-1,3-thiazolidin-3-yl) ethanesulfonic acid) as an active ingredient, thereby treating Parkinson's disease in the subject.

2. The method of claim 1, wherein the STT interacts with a TPP domain of DUSP10.

3. The method of claim 1, wherein the STT inhibits ROS production.

4. A method for treating Parkinson's disease in a subject in need of treatment, the method comprising administering to the subject a composition comprising a DUSP10 protein or a polynucleotide encoding the DUSP10 protein as an active ingredient, thereby treating Parkinson's disease in the subject.

* * * * *

SEQUENCE LISTING

```
<160> NUMBER OF SEQ ID NOS: 2

<210> SEQ ID NO 1
<211> LENGTH: 482
<212> TYPE: PRT
<213> ORGANISM: Artificial Sequence
<220> FEATURE:
<223> OTHER INFORMATION: Dusp10 NP_009138.1

<400> SEQUENCE: 1

Met Pro Pro Ser Pro Leu Asp Asp Arg Val Val Val Ala Leu Ser Arg
1               5                   10                  15

Pro Val Arg Pro Gln Asp Leu Asn Leu Cys Leu Asp Ser Ser Tyr Leu
            20                  25                  30

Gly Ser Ala Asn Pro Gly Ser Asn Ser His Pro Pro Val Ile Ala Thr
        35                  40                  45

Thr Val Val Ser Leu Lys Ala Ala Asn Leu Thr Tyr Met Pro Ser Ser
    50                  55                  60
```

-continued

```
Ser Gly Ser Ala Arg Ser Leu Asn Cys Gly Cys Ser Ser Ala Ser Cys
 65                  70                  75                  80

Cys Thr Val Ala Thr Tyr Asp Lys Asp Asn Gln Ala Gln Thr Gln Ala
                 85                  90                  95

Ile Ala Ala Gly Thr Thr Thr Thr Ala Ile Gly Thr Ser Thr Thr Cys
            100                 105                 110

Pro Ala Asn Gln Met Val Asn Asn Glu Asn Thr Gly Ser Leu Ser
        115                 120                 125

Pro Ser Ser Gly Val Gly Ser Pro Val Ser Gly Thr Pro Lys Gln Leu
        130                 135                 140

Ala Ser Ile Lys Ile Ile Tyr Pro Asn Asp Leu Ala Lys Lys Met Thr
145                 150                 155                 160

Lys Cys Ser Lys Ser His Leu Pro Ser Gln Gly Pro Val Ile Ile Asp
                165                 170                 175

Cys Arg Pro Phe Met Glu Tyr Asn Lys Ser His Ile Gln Gly Ala Val
                180                 185                 190

His Ile Asn Cys Ala Asp Lys Ile Ser Arg Arg Leu Gln Gln Gly
        195                 200                 205

Lys Ile Thr Val Leu Asp Leu Ile Ser Cys Arg Glu Gly Lys Asp Ser
        210                 215                 220

Phe Lys Arg Ile Phe Ser Lys Glu Ile Ile Val Tyr Asp Glu Asn Thr
225                 230                 235                 240

Asn Glu Pro Ser Arg Val Met Pro Ser Gln Pro Leu His Ile Val Leu
                245                 250                 255

Glu Ser Leu Lys Arg Glu Gly Lys Glu Pro Leu Val Leu Lys Gly Gly
                260                 265                 270

Leu Ser Ser Phe Lys Gln Asn His Glu Asn Leu Cys Asp Asn Ser Leu
        275                 280                 285

Gln Leu Gln Glu Cys Arg Glu Val Gly Gly Gly Ala Ser Ala Ala Ser
        290                 295                 300

Ser Leu Leu Pro Gln Pro Ile Pro Thr Thr Pro Asp Ile Glu Asn Ala
305                 310                 315                 320

Glu Leu Thr Pro Ile Leu Pro Phe Leu Phe Leu Gly Asn Glu Gln Asp
                325                 330                 335

Ala Gln Asp Leu Asp Thr Met Gln Arg Leu Asn Ile Gly Tyr Val Ile
            340                 345                 350

Asn Val Thr Thr His Leu Pro Leu Tyr His Tyr Glu Lys Gly Leu Phe
        355                 360                 365

Asn Tyr Lys Arg Leu Pro Ala Thr Asp Ser Asn Lys Gln Asn Leu Arg
        370                 375                 380

Gln Tyr Phe Glu Glu Ala Phe Glu Phe Ile Glu Glu Ala His Gln Cys
385                 390                 395                 400

Gly Lys Gly Leu Leu Ile His Cys Gln Ala Gly Val Ser Arg Ser Ala
                405                 410                 415

Thr Ile Val Ile Ala Tyr Leu Met Lys His Thr Arg Met Thr Met Thr
            420                 425                 430

Asp Ala Tyr Lys Phe Val Lys Gly Lys Arg Pro Ile Ile Ser Pro Asn
        435                 440                 445

Leu Asn Phe Met Gly Gln Leu Glu Phe Glu Glu Asp Leu Asn Asn
        450                 455                 460

Gly Val Thr Pro Arg Ile Leu Thr Pro Lys Leu Met Gly Val Glu Thr
465                 470                 475                 480

Val Val
```

```
<210> SEQ ID NO 2
<211> LENGTH: 1449
<212> TYPE: DNA
<213> ORGANISM: Artificial Sequence
<220> FEATURE:
<223> OTHER INFORMATION: Dusp10 DNA

<400> SEQUENCE: 2
atgcctccgt ctcctttaga cgacagggta gtagtggcac tatctaggcc cgtccgacct      60
caggatctca acctttgttt agactctagt taccttggct ctgccaaccc aggcagtaac     120
agccaccctc ctgtcatcgc caccaccgtt gtgtccctca aggctgcgaa tctgacgtat     180
atgccctcat ccagcggctc tgcccgctcg ctgaattgtg gatgcagcag tgccagctgc     240
tgcactgtgg caacctacga caaggacaat caggcccaaa cccaagccat tgccgctggc     300
accaccacca ctgccatcgg aacctctacc acctgccctg ctaaccagat ggtcaacaat     360
aatgagaata caggctctct aagtccatca agtggggtgg gcagccctgt gtcagggacc     420
cccaagcagc tagccagcat caaaataatc taccccaatg acttggcaaa gaagatgacc     480
aaatgcagca gagtcaccct gccgagtcag ggccctgtca tcattgactg caggcccttc     540
atggagtaca acaagagtca catccaagga gctgtccaca ttaactgtgc cgataagatc     600
agccggcgga gactgcagca gggcaagatc actgtcctag acttgatttc ctgtagggaa     660
ggcaaggact ctttcaagag gatctttttcc aaagaaatta tagtttatga tgagaatacc     720
aatgaaccaa gccgagtgat gccctcccag ccacttcaca tagtcctcga gtccctgaag     780
agagaaggca aagaacctct ggtgttgaaa ggtggactta gtagttttaa gcagaaccat     840
gaaaacctct gtgacaactc cctccagctc caagagtgcc gggaggtggg gggcggcgca     900
tccgcggcct cgagcttgct acctcagccc atccccacca ccctgacat cgagaacgct     960 gagctcaccc ccatcttgcc cttcctgttc cttggcaatg agcaggatgc tcaggacctg    1020
gacaccatgc agcggctgaa catcggctac gtcatcaacg tcaccactca tcttcccctc    1080
taccactatg agaaaggcct gttcaactac aagcggctgc cagccactga cagcaacaag    1140
cagaacctgc ggcagtactt tgaagaggct tttgagttca ttgaggaagc tcaccagtgt    1200 gggaagggc ttctcatcca ctgccaggct ggggtgtccc gctccgccac catcgtcatc    1260
gcttacttga tgaagcacac tcggatgacc atgactgatg cttataaatt tgtcaaaggc    1320
aaacgaccaa ttatctcccc aaaccttaac ttcatggggc agttgctaga gttcgaggaa    1380
gacctaaaca acggtgtgac accgagaatc cttacaccaa agctgatggg cgtggagacg    1440
gttgtgtga                                                             1449
```